(12) United States Patent
Haimerl et al.

(10) Patent No.: US 8,165,366 B2
(45) Date of Patent: Apr. 24, 2012

(54) DETERMINING CORRESPONDENCE OBJECT PAIRS FOR MEDICAL NAVIGATION

(75) Inventors: Martin Haimerl, Gilching (DE); Frank Grünschläger, Feldkirchen (DE); Markus Hepke, München (DE); Oliver Fleig, Baldham (DE); Martin Haberl, München (DE)

(73) Assignee: BrainLAB AG, Feldkirchen (DE)

( * ) Notice: Subject to any disclaimer, the term of this patent is extended or adjusted under 35 U.S.C. 154(b) by 971 days.

(21) Appl. No.: 12/147,734

(22) Filed: Jun. 27, 2008

(65) Prior Publication Data
US 2009/0003673 A1    Jan. 1, 2009

Related U.S. Application Data

(60) Provisional application No. 60/950,703, filed on Jul. 19, 2007.

(30) Foreign Application Priority Data

Jun. 29, 2007 (EP) .................................. 07111415

(51) Int. Cl.
*G06K 9/00* (2006.01)

(52) U.S. Cl. ........................................ 382/128; 600/424

(58) Field of Classification Search .................. 382/128, 382/130–133, 287–289, 293, 294
See application file for complete search history.

(56) References Cited

U.S. PATENT DOCUMENTS

| 6,096,050 | A | 8/2000 | Audette |
| 8,090,168 | B2 * | 1/2012 | Washburn et al. ............ 382/128 |
| 2002/0049378 | A1 * | 4/2002 | Grzeszczuk et al. .......... 600/427 |
| 2002/0147455 | A1 | 10/2002 | Carson |
| 2004/0023309 | A1 * | 2/2004 | Noll ............................... 435/7.2 |

FOREIGN PATENT DOCUMENTS

| WO | 2006/048651 | 5/2006 |
| WO | 2006/106335 | 10/2006 |

\* cited by examiner

*Primary Examiner* — Clayton E LaBalle
*Assistant Examiner* — Leon W Rhodes, Jr.
(74) *Attorney, Agent, or Firm* — Renner, Otto, Boisselle & Sklar, LLP

(57) ABSTRACT

A system and method for determining the position of correspondence object pairs including A-objects and B-objects that represent the same objects of the same anatomical body structure in two different reference frames A and B, including: defining A-objects and B-objects that each represent different objects of the body structure in their respective reference frames; determining geometric relationship data A and geometric relationship data B that describe a geometric relationship between the A-objects based on positions of the A-objects in the reference frame A and the B-objects in the B reference frame; and providing data derived or extracted from the geometric relationship data A and from the geometric relationship data B to allow a comparison of a geometric relationship between at least two A-objects to a geometric relationship between at least two B-objects.

29 Claims, 3 Drawing Sheets

DETERMINING CORRESPONDENCE OBJECT PAIRS FOR MEDICAL NAVIGATION

RELATED APPLICATION DATA

This application claims priority of U.S. Provisional Application No. 60/950,703 filed on Jul. 19, 2007, and EP07111415 filed on Jun. 29, 2007, which are incorporated herein by reference in their entirety.

FIELD OF THE INVENTION

The invention relates to determining correspondence object pairs, which represent the same objects of the same anatomical body structure in different reference frames. The determined correspondence object pairs can be used to enable navigation relative to an anatomical body structure.

BACKGROUND OF THE INVENTION

A correspondence object pair describes the same object of an anatomical body structure in two different reference frames. So-called anatomical landmarks may be used as the objects since they are easy for the physician to identify in the anatomical body structure. In accordance with the invention, not only landmarks but any other objects, including parts of the anatomical structure or geometric primitives that have a specific relationship to the body structure (for example, points on the surface, objects of symmetry, tangential objects, fitted geometric objects) can be used to determine correspondence object pairs and to determine the spatial relationship between the two reference frames.

Prior to performing navigation relative to a body structure, there may be a (virtual) reference frame in which an anatomical body structure is three-dimensionally spatially described, based on medical analysis methods (for example, magnetic resonance tomography (MRT) or computer tomography (CT)). These analysis methods are typically performed at an earlier point in time (for example, pre-operatively) and provide detailed information concerning the body structure. This detailed information may be used for planning an operation. It may be desirable to compare the virtual reference frame (for example, the "virtual" data concerning the anatomical body structure on which the planning of an operation is based) with obtained "actual" body structure data, for example, intra-operatively. To this end, marker devices may be attached to the body structures of the patient, for example, to the bone. When detected, the marker devices allow actual body structure data to be obtained, the terms "actual" and "virtual" are used in the following to distinguish the aforesaid reference frames and the corresponding data and objects. The positional relationship between the anatomical body structure and the marker devices may not be known at the beginning of the operation. To compare the virtual reference frame with the actual reference frame, so-called landmarks on the body structure may be (intra-operatively) touched, using a pointer. Markers may be likewise attached to the pointer with known positions relative to the tip of the pointer. Therefore, the tip of the pointer and the position of the landmark can be detected by a marker detection device. The marker detection device also may detect the marker device attached to the body structure. The detection of the body structure marker device provides the relative position between the marker device and the tip of the pointer and, therefore, the relative position between the marker device and the landmark. At least three landmarks may be captured in the actual reference frame by the surgeon via the pointer and read into a navigation system. The same (corresponding) landmarks may be identified by the physician in the virtual reference frame. Using the determined pairs of corresponding landmarks (that represent an example of correspondence object pairs) it is possible to establish the spatial relationship between the actual reference frame and the virtual reference frame. The degree of accuracy of the special relationship may depend on the relative position of the landmarks. With this relationship established, it is possible to navigate an instrument (having a marker device) relative to the anatomical body structure, wherein the position of the instrument relative to the virtual body structure data can be viewed on a screen.

In reality, determining the landmarks can be difficult. Usually, only a small region of the anatomical body structure (for example, the bone structure) is exposed, such that only a few prominent surface shapes on the body structure (that can be used as landmarks) are available. In other words, if the surface structure of the bone is not prominent, landmark determination can become uncertain.

SUMMARY OF THE INVENTION

The present invention relates to determining correspondence object pairs that can be used to compare different reference frames. These two reference frames are referred to in the following as reference frame A and reference frame B. Reference frame A, for example, can be the virtual reference frame, and reference frame B can be the actual reference frame. Alternatively, reference frame B can be the virtual reference frame and reference frame A can be the actual reference frame. The order and sequence in which an object is determined in a reference frame A (as an A-object) and in a reference frame B (as a B-object) is arbitrary. Whenever a first and second object are mentioned in the following, it may be assumed that the two objects are different and represent different parts of the body structure.

In accordance with the invention, geometric relationships between two or more objects in a first reference frame may be used to localize corresponding objects in the other, second reference frame. The localization may be based on the geometric relationships between the objects in the first reference frame. If the objects are corresponding, it may be assumed that the geometric relationships between the objects can be compared in the two reference frames.

For example, if (two) A-objects are defined in reference frame A and (two) B-objects are defined in reference frame B, the geometric relationship between the objects in their respective reference frames can be determined (calculated) using the positions of the objects in their respective reference frames. These geometric relationships are referred to as relationship data A for reference frame A and relationship data B for reference frame B. The relationship data A and relationship data B together represent comparative data that enables a comparison between relationship data A and relationship data B. For example, both the relationship data A and the relationship data B can be displayed and the distance between two A-objects and the distance between two B-objects can be displayed. If the distances correspond, then the operator (for example, a physician) can assume that he has correctly determined the two corresponding object pairs.

One or more correspondence object pairs may be determined with the aid of the comparative data (automatically or using an input device) based on the defined A-objects and B-objects. In this example, at least three object pairs are used. The pairs can be automatically determined based on a comparison of the relationship data. For example, the deviation between the relationship data may be within a predetermined value. Alternatively or additionally, an operator can determine pairs of corresponding objects, by determining defined objects (for example, an A-object and a B-object) as corresponding objects. The method in accordance with the invention may assist with the determination of the position of correspondence object pairs, and also in the determination of the correspondence object pairs. If the number of determined pairs of corresponding objects is not sufficient to accurately determine the relationship between the two reference frames, then the relationship between the two reference frames can be provisionally determined based on the presently determined object pairs. For example, the spatial relationship may be based on one corresponding object pair or two corresponding object pairs, providing at least three correspondence object pairs have already been determined or provisionally determined. Based on this partial determination (also referred to herein as alignment or partial registration) of the A-objects in the reference frame B and/or of the B-objects in the reference frame A, reference information may be calculated for an operator. The reference information may be, for example, based on points, lines, areas or delineated spaces that represent regions for potential correspondence object pairs. Using the reference information, an operator may receive an acoustic and/or visual indication that he is or is not situated in a certain region and/or how far away he is from such a region. Thus, in accordance with the invention, aligning the two reference frames based on one or more given correspondence object pairs enables the reference information to be refined and configured to be more comprehensible to an operator.

To refine the reference information and acquire additional information for a user, the A-objects, B-objects and/or auxiliary objects (discussed further below) can be alternatively or additionally transformed or projected into a common coordinate space. This common coordinate space is not necessarily a geometric space, but can be a feature space. A feature space arises if the aforesaid objects are subjected to a Fourier transformation or shape analysis to be able to acquire additional comparative data (for example, comparative values in the coordinate space).

If the operator is not satisfied with the level of correspondence between the relationship data, he can change the position of the objects in the respective reference frames and/or replace them with new objects, until he is satisfied with the level of correspondence between relationship data A and relationship data B. The operator may change and/or replace those objects that are difficult to identify on the body structure as landmarks and that are thus associated with a greater level of uncertainty.

Comparative data may be provided that includes the geometric relationship data A and the geometric relationship data B and enables data A and data B to be compared. The comparative data may be used in subsequent steps, for example, to produce reference information for an operator that displays both the relationship data A and the relationship data B. The data may be displayed to compare the comparative data and to display the result of comparison (the comparative value) within the context of reference information. The comparative data also can be used to manually or automatically replace A-objects and/or B-objects. The data also can be used to change the position of A-objects and/or B-objects automatically, and/or to guide a change in A-objects and/or B-objects using reference information. The comparative data may be used to check whether the defined A-objects and/or B-objects are suitable for a correspondence object pair and/or whether defined object pairs satisfy a consistency check. A plurality of calculated comparative values may be combined to produce an additional comparative value. A combination of the comparison of the distances and a comparison of angular relationships can be adduced, for example, to determine a comparative value. A comparative value may be produced by multiplying two comparative values or selected from a group as a maximum, minimum, or average value of comparative values. The value may be used as a basis for reference information for the operator, or on the basis of which a correspondence object pair is automatically selected. It is also possible to select only one comparative value from various comparative values. For example, a comparative value that is based on an angular relationship may be selected, but not one that relates to a distance. The selected value can be defined depending on the given situation, to obtain as stable and reliable a comparative value as possible.

When changing the position of one of the objects (A-object or B-object) or when replacing an object with a new object, the operator may be assisted by reference information that is based on the comparative data. The position of the other objects that are not to be replaced or changed is assumed to be given, and the reference information gives an indication of the extent to which the relationship data A and the relationship data B correspond. It is possible to indicate (e.g., acoustically) when the two relationship data sets approach each other or move further away from each other with regard to the comparative value. If the object is a virtual object, then based on the geometric relationship data in the actual space, it is possible to display a selection of virtual candidate objects that would correspond to the relationship data in the actual space. For example, if a particular distance is predetermined (as actual relationship data) by two objects in the actual space, and if only one object is predetermined in the virtual space, then candidate objects in the virtual space lie on the surface of a sphere. This sphere is defined by a center that corresponds to the object already determined in the virtual space and a radius that corresponds to the distance between the two objects in the actual space. More specifically, the candidate objects may lie on points or along a line or lines that result from an intersection between the surface of the sphere and the surface of the body structure. The indicated information (for example, a displayed surface of the sphere, or in two dimensions, a circular line or intersection points or intersection lines) may be helpful when the object to be defined lies on a substantially one-dimensional body structure. For example, the object may lie on a ridge-like body structure or on an edge of a body structure, and the surface of the sphere intersects the course and surface of said ridge or the edge at an angle. In this example, the results include punctiform candidate objects between which the operator can then choose. Furthermore, due to a provisional registration between the virtual and actual object (based on the relationship data available) it is possible to display the alignment of the objects on a screen for the operator. It is therefore possible, while the objects are being changed, to facilitate spatial orientation and therefore also make it easier to localize the objects.

The aforesaid sphere or surface of the sphere represents an example of an auxiliary object that can be used to generate reference information. The sphere can be displayed on a screen if it is a sphere in the virtual space, or the operator can be guided by reference information when capturing subsequent objects in the actual space, based on the spherical shape. For calculating auxiliary objects, an automatic and/or interactive method can be used for defining particular objects that have, for example, a predetermined relationship to the anatomical body structure or to the defined A-objects and/or B-objects. The objects can be geometric base bodies such as spheres, cuboids, lines, polygons, etc. Furthermore, the auxiliary objects can be regions in the virtual (or actual space)

that are defined by the fact that the comparative value of all the objects in the region in relation to a selection of given objects (and/or body structures) assumes a particular value (or is within a particular range of values). In the example of the surface of the sphere mentioned above, this region contains those points that have a fixed distance calculated from the relationship data. As a result, the surface of the sphere can be intersected by the anatomical body structure, to further restrict the selection points and to obtain a more specific construction of the auxiliary objects.

Auxiliary objects can be defined by fitting geometric structures into at least parts of the anatomical structure. A tangent can be placed onto the ridge of a bone structure (for example, the front edge of the acromion), or a plane can be fitted to the glenoid surface. Another example could be fitting a sphere into the recess circumscribed by the glenoid surface. The aforesaid comparative values and/or comparative data also can be adduced to determine the auxiliary objects. For example, the objects could be chosen to achieve the optimum comparative values, wherein the comparative values may be determined such that the geometric properties of the auxiliary objects in reference frame A and in reference frame B may be compared with each other. A sphere, for example, can be fitted in each of the two reference frames, and the diameters of the spheres may be compared. Geometric relationship data between auxiliary objects in the two reference frames also can be determined from the geometric relationship between different auxiliary objects, for example, an angular relationship between two planes. This geometric relationship data can be compared to acquire a comparative value.

There are various ways to determine correspondence object pairs. For example, a multitude of A-objects and B-objects can be defined such that, in their respective pairs, they represent candidates for correspondence object pairs. From this multitude of candidate objects, those pairs may be selected, by the operator or automatically, that provide the best level of correspondence between the geometric relationship data (relationship data A and relationship data B).

Alternatively, it is also possible to proceed in steps. For example, a portion of the A-objects and B-objects defined can be assumed to be provisional correspondence object pairs. It is possible to begin even with a single pair consisting of one A-object and one B-object. This single pair is preferably a pair based on a particularly prominent and easy-to-determine landmark. Another object can be selected in one of the two reference frames. (To this end, it is also possible to refer to database information that contains information concerning typical distances and positional relationships between the first selected landmark and the second landmark to be determined.) Based on this object selection or information, the probable region for the second landmark can be visually highlighted in a display. An operator then selects the second landmark. Based on the geometric relationship between the first and second landmark (in the actual or virtual space), determining the second landmark in the other space in each case (the virtual or actual space) can be made using the reference information (comparative data). The determined objects can be assumed to be at least provisional correspondence pairs, based upon which other correspondence pairs may be determined.

If a plurality of correspondence pairs (for example, at least three correspondence pairs) are given, then consistency checks may be performed. Consistency checks may be used to check whether object pairs, each consisting of one A-object and one B-object, that have previously been defined (at least provisionally) as correspondence object pairs, exhibit a good level of correspondence between the geometric relationship data. This correspondence should be checked not only with respect to a subsequent object pair, but also with respect to other object pairs (determined in the interim). (A good level of correspondence may be, for example, a level of correspondence that is within a predetermined value.) If, for example:

three object pairs are determined,
the object pair one and two were determined based on the fact that the geometric relationship between the first A-object and the second A-object corresponds to the geometric relationship between the first B-object and the second B-object, and
the third object pair was determined such that the geometric relationship between the second A-object and the third A-object corresponds to the geometric relationship between the second B-object and the third B-object, then this correspondence can be checked using a consistency check. The geometric relationship between the first A-object and the third A-object may be compared with the geometric relationship between the first B-object and the third B-object. If this comparison results in a good level of correspondence, then the three object pairs may be defined as correspondence object pairs. If the level of correspondence is unsatisfactory, or if one still wishes to determine additional object pairs, then the object pairs can be regarded as candidate object pairs, wherein the individual A-objects and B-objects can be changed to acquire a better level of correspondence between the geometric relationship data. For this purpose, previously defined objects can be replaced with new objects, or the position of defined objects can be changed. In the virtual space, this change may be achieved by translating an object on the screen using a mouse. In the actual space, this change can be achieved by moving the pointer from one surface point on the body structure to another surface point.

The points can additionally be checked with regard to their consistency. If at least three landmarks have been captured, the determining consistency (for example, the distance between points) may be checked by cyclically checking from object to object and adjusting object positions as applicable. This method for checking the consistency can be improved if more than three objects are defined. For example, objects can be redefined, or the position of the objects can be changed. The sequence of defining objects can follow a predetermined plan.

The method may be configured such that an operator is automatically requested to change objects or input new objects that are intended to represent an additional object or to replace existing objects. This automatic request may occur when a comparison of the relationship data A with the relationship data B (for example, based on the comparative data) does not lead to a satisfactory result. The request also may occur when an automatic check determines that the relationship data does not fulfill predetermined criteria. Such criteria may be given if all the objects previously defined in their respective reference frames lie substantially on a straight line, wherein "substantially" means, for example, that they lie within a predetermined cylinder, the radius of which measures less than 30% of the length of the cylinder. For greater precision, a value of less than 10% of the length of the cylinder may be required. In such cases, it may be assumed that the spatial relationship between the virtual and actual space cannot yet be determined to a sufficient level of certainty from the previously determined correspondence object pairs.

Another example may be if the previously determined objects in one of the two spaces lie substantially on one plane. Here, "substantially" means, for example, that a space in which the defined objects that form the plane lie within a predetermined thickness that measures less than 20% of the distance between the most distant objects. For greater precision, a value of less than 10% of the distance between the most distant objects may be required. As an alternative to the aforesaid criteria, it is possible to introduce additional absolute criteria based on the detection accuracy of the marker devices or the scaling accuracy of the analysis data on which the virtually represented body structures are based. For example, the aforesaid thickness of the described space or the aforesaid radius of the cylinder may be selected as 5 mm to 1 cm or another suitable criteria. Thus, a sufficient number of parameters relating to the spatial relationship between the reference frames are to be determined from the determined object pairs to clearly define the spatial relationship between the aforesaid spaces. These parameters (for example, distances between objects, angles between lines that connect objects, angles between planes formed by objects, etc.) may be referred to as degrees of freedom. Determination additional objects may be required if it is not possible to determine (to a sufficient level of accuracy) all the degrees of freedom relating to the spatial relationship between the two reference frames.

The input of additional objects and the comparison can be performed automatically. For example, the geometric relationship data A and relationship data B can be automatically compared. The distance between two A-objects can be automatically compared with the distance between two B-objects. If a good level of correspondence is found (for example, the distances correspond within a predetermined percentage range of ±10%) and/or if the deviation is smaller than a predetermined absolute amount that is smaller than 1 cm, then an indicating signal is provided. It is understood that the predetermined percentage may be tightened to ±1% or the absolute values may be tightened to 5 mm or even 1 mm, if appropriate for the procedure to be performed.

Alternatively or additionally, the position of an object can be automatically changed based on the result of comparison. For example, if two actual objects and two virtual objects are predetermined, the position of one of the two virtual objects (or both virtual objects) can be automatically changed based on the result of comparison, until a good level of correspondence between the relationship data is achieved. Changes in the position of an object may be made by using the positions of the virtual objects that are already given (for example, by an operator) but that are associated with a level of inaccuracy. In the aforesaid example, the position or positions can be changed such that the position of an object is (automatically) changed along the surface of the body structure, such that it is moved toward or away from the other object, depending on the direction that produces a better level of correspondence. An additional constraint also can be introduced when automatically changing the position, for example, moving the object along an edge or the line of a ridge in the body structure, to change the position.

If satisfactory results are not achieved, the operator may be required to change the position of the actual object (or also the position of the virtual object). By using an iterative procedure (for example, by changing the position of different actual and/or virtual objects), it is possible to improve the level of correspondence between the corresponding relationship data and to acquire good consistency. If a certain plan is predetermined with respect to the order in which particular landmarks are to be determined, then correspondence pairs can be determined in different patients in a highly comparative way, such that the comparability of operational results is increased. This comparability furthers the reliability of statistically collected data concerning the course of the operation, and increases the level of certainty for the physician in determining landmarks.

A system and method in accordance with the invention allows the capture of objects (for example, landmarks) to be optimized, and allows defining objects and/or landmarks to determine the correspondence object pairs to be optimized. For example, if a landmark that can be very accurately determined is given as the starting point, it is possible to optimize the determination of other landmarks (objects). If objects (for example, other landmarks) lie on an edge of the surface of the body structure, there may be a single degree of freedom left for capturing the object, namely along the edge and/or ridge. The distance between the objects may be the criterion for defining the remaining degree of freedom. The object should lie on the intersection point between the edge and a surface of a sphere that has the first landmark as its center and the distance between the planned landmarks as its radius. Care should be taken that the orientation of the edge is not identical (or nearly identical) to the direction between the landmarks (objects).

If two objects (landmarks) have already been captured, it is possible in accordance with the invention to proceed as follows. The capture of the third landmark can be guided by showing the distances from the two previously defined objects (landmarks). The remaining degree of freedom can be set if the object lies on the surface of the body structure. The object should lie at the intersection point of the surface of the body structure and the two surfaces of the spheres. The surfaces of the spheres should have the first landmarks as their centers and the distances between the planned landmarks as their respective radii.

In many cases (for example, registering the pelvis in a lateral position in hip operations, registering the scapula in shoulder operations, or registering vertebrae in minimally invasive spinal operations), it is difficult to define reproducible landmarks to a sufficient level of accuracy. The system and method in accordance with the invention allows generation of a plurality of reproducible landmarks. This procedure may be based on pre-captured information (analysis data) and on geometric and/or topological properties of the surface of the body structure. The procedure may provide assisting information or helpful guidance references for a physician to reproducibly determine said landmarks. The registration process may be more robust and more stable when a plurality of landmarks and/or objects are used.

The method in accordance with the invention assists the physician in determining landmarks, since the physician can be given direct feedback as to how well he has defined the landmarks and whether a defined landmark is consistent with the previously defined landmarks. In the prior art, when landmarks are freely determined by a physician there can be significant differences (for example, 10 to 15 mm) between the captured objects and/or landmarks and the planned objects and/or landmarks. The method in accordance with the invention allows the level of accuracy in defining correspondence object pairs and landmarks to be increased. As mentioned above, the method and system in accordance with the invention may be used to capture (in the actual space) or define (in the virtual space) objects in a registration process (for example, specific landmarks) such as are used in medical navigation. The system assists the surgeon in capturing and/or defining objects, by showing and/or (automatically) using information that is already available. The information can be displayed on a computer monitor and/or also acoustically indicated, or it can be automatically used in an algorithm (program) for defining landmarks and/or objects.

A comparative value may be a measure of the deviation from each other of relationship data A and relationship data B. For example, this value could be the distance between points, distances from points or lines and/or general geometric distances, angular deviations, distance deviations, or angular deviations in projections. The comparative value can be any comparative value calculated by an algorithm, wherein the algorithms may be:

algorithms for aligning (for example, registration between the A-object and the B-object based on correspondence information already available); or algorithms for comparing the structures in a suitable mathematical representation (for example, a transformation into a suitable coordinate system, as applicable taking into account weightings of the individual coordinate components).

Additionally, the method and system in accordance with the invention can be used to control the workflow during the capture process by checking the consistency of the captured objects on the basis of specified criteria.

In accordance with one exemplary embodiment of the invention, the criterion is valid between some pairs or between each pair of a sequence or ordered list of objects. A value that represents the consistency can be displayed on a monitor or indicated acoustically. The aforesaid comparative values (that are, for example, valid between different object pairs) can be mathematically processed to calculate a value for a consistency. An average comparative value of all the determined comparative values, or the maximum comparative value that may represent a maximum deviation of the relationship data A from the relationship data B, can be adduced as a consistency value. For example, if it is assumed that:

there is a good comparative value for the relationship between the first and second object pair (for example, a small difference in the distances);

there is a good comparative value for the relationship between the second and third object pair (for example, a small difference in the distances); and there is a poor comparative value between the first and third object pair (for example, a large difference between the distances);

then this maximum comparative value exhibiting the greatest difference can be adduced as the criterion for consistency (e.g., the consistency value). Alternatively, the average value of the difference or another combination of the comparative values can be determined as the consistency value.

Alternatively or additionally, the system can automatically request that objects be recaptured if the consistency is found to be insufficient or is regarded by the operator as being insufficient.

The capture of objects here means, for example, any method for obtaining coordinate information concerning objects (for example, landmarks). Such capturing may be necessary in an intra-operative situation. Capturing landmarks may constitute capturing coordinates relative to a marker device (for example, the reference star fixed to a bone). The capture may be performed by any device or any method for capturing positional information concerning the position of an object. To capture the positional information, a capture device may include any of the following:

the aforesaid marker device affixed to, for example, a pointer;

a calibrated instrument (for example, with a marker device attached to it); and a detection device (such as a camera) for detecting the marker device and for forwarding the detection signals to a computer.

Points or objects can be defined in registered image data (for example, fluoroscopic images). Image data may be registered when the image dots that the data describes can be assigned a spatial position in a reference frame that is stationary with respect to a marker device attached to a body structure (and for example, used for navigation). Capturing image data (fluoroscopic images) represents another example of intra-operatively employed analysis methods. With fluoroscopic images, actual objects can be determined in the actual space relative to a marker device. The captured image data may be provided to a computer in accordance with the invention. The marker device also may be captured by the intra-operative analysis device, such that the analysis device detects both the marker device and the body structure (and therefore the actual objects) to enable registration. Thus, in this example, the capture device may include the analysis device and the marker device.

In accordance with an exemplary method, a plurality of objects can be captured such that the objects most suitable for forming correspondence object pairs are automatically selected. The automatic selection can, for example, be based on the distance between the objects. The automatic selection can be made immediately (e.g., following the object capture) or subsequently (e.g., during a registration process).

Defining objects and/or landmarks herein means any method for capturing information concerning landmarks and/or objects in a given three-dimensional model of a body structure or of a part of a body structure. The landmarks and/or objects can be defined automatically or manually. The captured information can be used as an additional constraint for automatically defining the landmarks. The three-dimensional model can be a part of a three-dimensional image data set of a body structure that has been obtained using CT or MRT, or also can be any other three-dimensional representation of the part of the body structure (for example, a statistical model, a generic model, or a fitted model of the body structure or also a three-dimensional model captured by a laser scanner).

The registered image data can be used in navigation-assisted operations in the field of medicine. Surgical incisions that require a high level of precision can be precisely planned beforehand and then performed with image assistance. For this purpose, a navigated treatment apparatus (for example, a drill) may be provided with a so-called marker device. This marker device on the treatment apparatus is captured by a camera system along with another marker device that is situated at a known spatial position (for example, fixed to a body structure). The relative position between the marker device on the treatment apparatus and the second marker device is ascertained. From this relative position, a position of the treatment apparatus is determined. During the operation, a registered image data set may be displayed, in which the current position of the treatment apparatus is simultaneously displayed.

There are many different image data sets, on the basis of which it is possible to navigate. For example, it is possible to navigate based on the registered two-dimensional image data sets (for example, based on the conventional x-ray recordings). It is also possible to navigate based on the registered three-dimensional image data sets that are, for example, generated in a computer tomography (CT) or magnetic resonance (MRT) recording. In the case of three-dimensional image data sets, the surgeon may be shown sectional representations through different planes. Virtual body structure data (that has been pre-operatively obtained) likewise may be accurately registered by comparing the actual reference frame with the virtual reference frame, and used in navigation.

BRIEF DESCRIPTION OF THE DRAWINGS

The forgoing and other features of the invention are hereinafter discussed with reference to the figures.

FIG. 1a shows two planned (virtual) landmarks and FIG. 1b shows the capture of two corresponding actual landmarks.

FIG. 2a relates to a virtual reference frame and FIG. 2b relates to an actual reference frame.

DETAILED DESCRIPTION

Figure 1B:
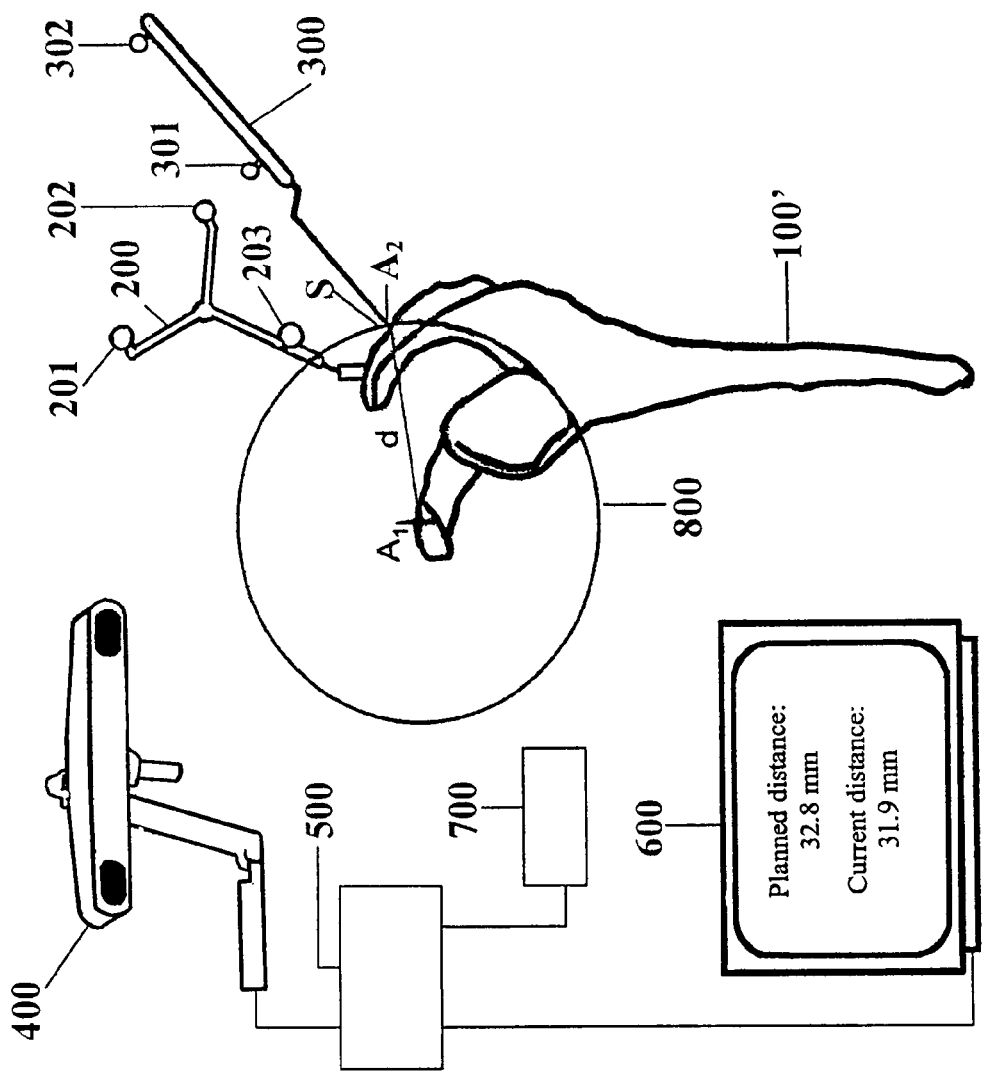
FIGS. 1a and 1b show landmarks being captured.
Figure 1A:
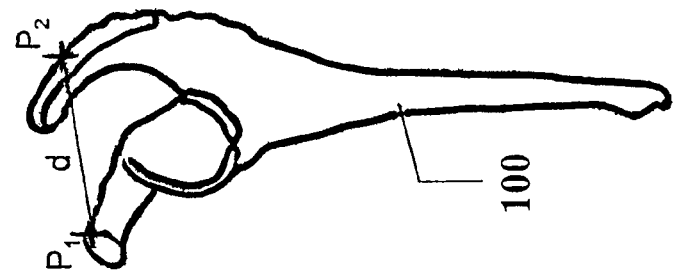

In the following exemplary embodiment, it is assumed that CT data is available as virtual data of the body structure and it is assumed that first and second landmarks have already been planned (e.g., defined in the virtual space based on the CT data). These first and second landmarks $P_1$ and $P_2$ are shown in FIG. 1a and are spaced by a line "d". Since CT-based registration is a rigid registration, the distances (for example, the relative distance relationships) are maintained. The distances between the landmarks on the actual body structure, which may be determined intra-operatively, should be the same for the corresponding landmarks. A virtual body structure 100 in FIG. 1a corresponds to an actual body structure 100' in FIG. 1b. A marker device 200 (e.g., a reference star) is attached to the actual body structure 100' and is provided with markers (e.g., marker spheres) 201, 202 and 203 that may have predetermined positional relationships to each other. A pointer 300, that likewise comprises two markers (marker spheres) 301 and 302, is also shown in FIG. 1b. The markers (marker spheres) reflect or emit light (for example, infrared light) that is captured by a detection device 400 that may be connected to a computer 500 having a corresponding monitor 600. The detection device 400, the computer 500, and the monitor 600, are parts of a navigation system in accordance with the invention for assisting in determining correspondence object pairs. The positional relationships between the markers (marker spheres) may be stored in a database of the computer 500. The positional relationships between a pointer tip S and the markers (marker spheres) 301, 302 also may be stored in the database. The reference star 200 is fixed with respect to the body structure 100' and may be, for example, screwed into it. In the present example, it may be assumed that a landmark $A_1$ on the actual body structure 100' in actual space has already been captured and/or read into the system using the pointer 300. The position of the landmark $A_1$ relative to the reference star 200, therefore, may be known to the system. The position of $A_1$, for example, can be provided to the system by guiding the tip of the pointer 300 to the point $A_1$ and, using an input device 700 (for example, a mouse or keyboard) to inform the system that the tip S of the pointer is at landmark $A_1$. $A_1$ should correspond to the planned landmark $P_1$ and together with it should form a correspondence object pair. The distance d is known from the geometric relationship data of the planned landmarks $P_1$ and $P_2$. Thus, a multitude of possible (candidate) landmarks situated on the surface of a sphere 800 exhibiting the radius d exist for a landmark $A_2$ that corresponds to the planned landmark $P_2$ in the present example. The operator (for example, a physician) then knows that the planned landmark $P_2$ should be situated on top of the ridge of the body structure (the front edge of the acromion). Via the monitor 600, the operator also may be shown both the planned (virtual) distance d (32.8 mm in the example) and the current (actual) distance between the pointer tip S and $A_1$ (in the example, 31.9 mm). By moving the pointer tip S along the ridge of the body structure and observing the display on the monitor, the operator can then choose a point (for example, using the input device) as the corresponding point $A_2$ for which the planned distance corresponds as accurately as possible to the current distance and that is the actual location of the pointer tip S at the time of choosing.

Alternatively or additionally, the difference between the planned (virtual) distance and the current (actual) distance (the tip of the pointer) also can be displayed. The tip S of the pointer thus represents an example of a point on an object in the actual space. The method in accordance with the invention can be configured such that the tip of the pointer only represents such a point point when the pointer is touching the body structure 100' and/or when a corresponding input is made (for example, using an input device 700) and/or when the operator desires reference information (for example, on the monitor 600).

If the planned distance does not completely correspond to the current distance, an automatic correction also can be made in accordance with the invention, such that a better correspondence is achieved. To this end, the objects (points) $P_1$ and/or $P_2$ also can be translated.

As stated previously, two actual objects (points) can be captured first, and then the two corresponding planned (virtual) objects (points) defined. Capturing and defining objects and/or landmarks can be mixed or applied iteratively. The position of captured (actual) and/or defined (virtual) landmarks can be changed or readjusted, automatically or guided by an operator. These changes can be repeated until a preselected consistency is determined.

Figure 2B:
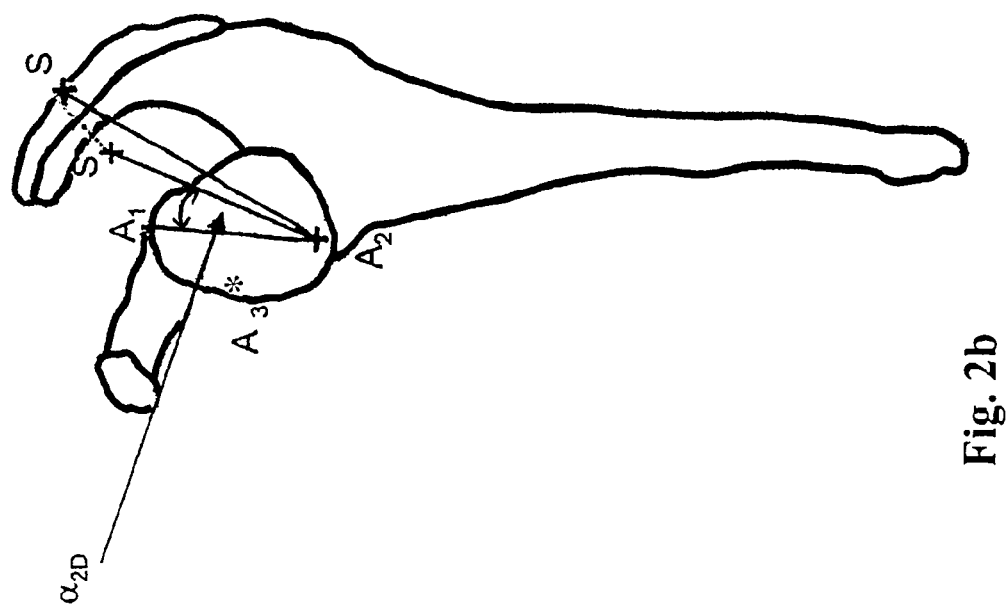
FIGS. 2a and 2b show objects being projected into a plane.
Figure 2A:
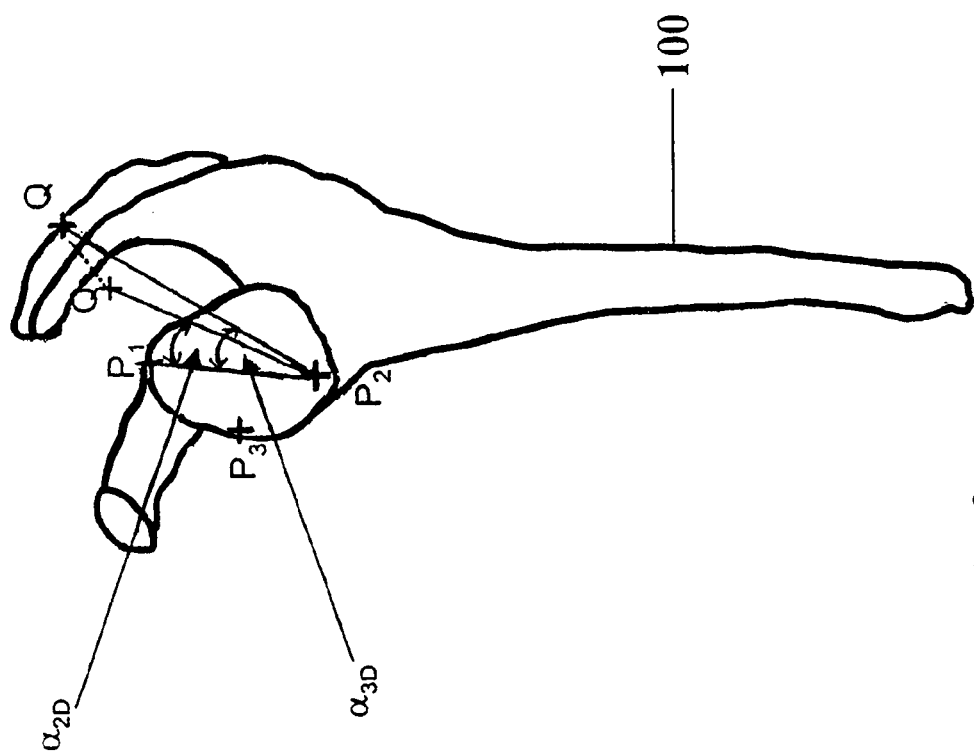

The virtual body structure 100 also is shown in FIGS. 2a and 2b. Landmarks $P_1$, $P_2$ and $P_3$ lie on the rim of a body structure (glenoid surface) and they form a plane. It is possible to define, as the geometric relationship, not only the relationship between $P_3$ and $P_2$ or between $P_3$ and $P_1$ but also the geometric relationship between $P_3$ and a connecting line between $P_1$ and $P_2$. For example, the landmark $P_3$ can be projected onto the connecting line, and the intersection point between the projection line and the connecting line between $P_1$ and $P_2$ can be used as the geometric relationship. This relationship can be used to guide an operator in determining the actual object corresponding to $P_3$.

The level of accuracy in comparing the reference frames can be increased if the points do not all lie in one plane. It may be desirable, in the example shown in FIG. 2a, to have landmarks not only in one plane, (e.g., the landmarks $P_1$, $P_2$ and $P_3$) but also a landmark that protrudes out of this plane. This landmark is identified in FIG. 2a by Q. Geometric relationship then data can be defined via the distances between Q and one of the points P. Geometric relationship data, however, also can be defined via angular relationships (identified in FIG. 2a by $\alpha_{2D}$ and $\alpha_{3D}$). $\alpha_{3D}$ represents a spatial angle between the connecting line from $P_1$ to $P_2$ and the connecting line from $P_2$ to Q. If this angle $\alpha_{3D}$, however, is used as the geometric relationship data, because of its three degrees of freedom it is associated with a greater level of uncertainty than the angle $\alpha_{2D}$ that lies in the plane defined by the points $P_1$ and $P_2$ and $P_3$ (the plane represents an example of an auxiliary object). In accordance with the invention, the uncertainty may be reduced by projecting the point Q into the aforesaid plane, where it represents the point Q*. This angular relationship of the virtual point Q* in the aforesaid plane then can be used to determine an actual landmark corresponding to Q, wherein it is assumed that actual objects $A_1$, $A_2$, $A_3$ (FIG. 2b) corresponding to the points $P_1$, $P_2$ and $P_3$ (FIG. 2a) have already been determined. The plane defined by the points $A_1$, $A_2$ and $A_3$ may be constructed as the auxiliary object corresponding to the plane given by the points $P_1$, $P_2$ and $P_3$. The tip of the pointer S may be moved and the tip is projected as S* into the plane defined by the actual objects $A_1$, $A_2$ and $A_3$. If the tip of the pointer S is moved thereby changing $\alpha_{3D}$, in the actual space, an angle corresponding to the angle $\alpha_{2D}$ is also changed in the actual space. When the angle $\alpha_{2D}$ in the actual space reaches angle $\alpha_{2D}$ in the virtual space, the position of the tip S of the pointer should be located at the position of the actual object corresponding to the virtual object Q. While the tip of the pointer is being moved, the actual angle can be displayed and/or the difference between the virtual angle $\alpha_{2D}$ and the corresponding actual angle can be displayed as a guidance reference for the operator.

In an alternative example, if the object $A_3$ has not yet been determined in the actual space but $A_1$, $A_2$, and S are determined, the following exemplary method can be used to determine corresponding points. The body structures can be aligned (provisionally registered) based on the points $P_1$, $P_2$ and Q in the virtual space and $A_1$, $A_2$ and S in the actual space. In this example, the alignment may be acquired by mapping the points $P_1$, $P_2$ and Q onto $A_1$, $A_2$ and S as optimally as possible. Using this provisional registration, it is possible to construct a point $A'_3$ in the actual space, for which a correspondence relationship to the point $P_3$ is established. Using the points $P_1$, $P_2$ and $P_3$ and $A_1$, $A_2$ and $A'_3$, it is possible to construct corresponding planes as auxiliary objects, that are used for projecting from Q and/or S, to determine points Q* and S*. The difference in the two-dimensional angles between the connecting lines $P_1P_2$ and $P_2Q^*$ in the virtual space and $A_1A_2$ and $A_2S^*$ in the actual space, respectively, then can be used as guidance information.

Figure 3:
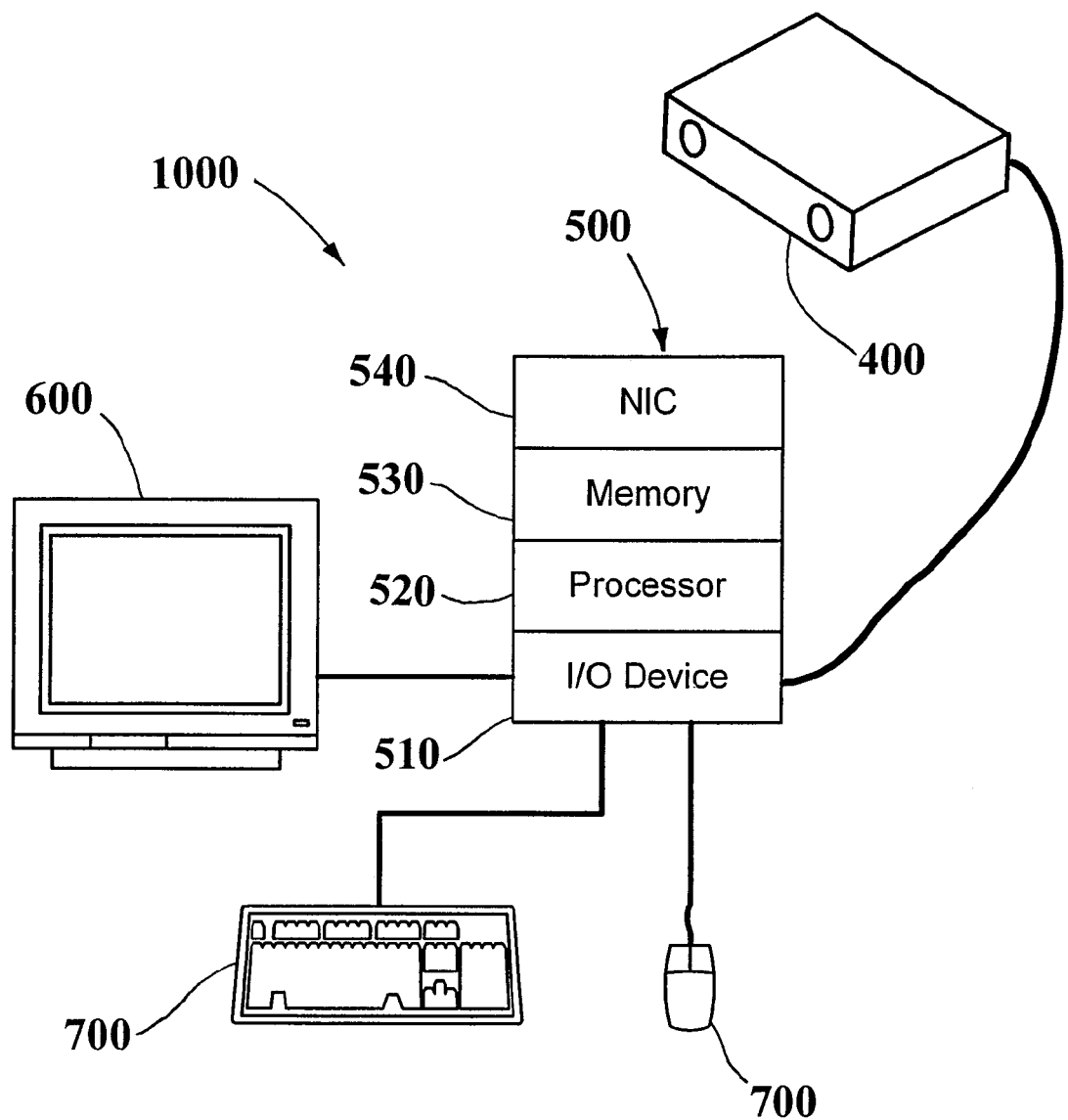
FIG. 3 shows a block diagram of an exemplary computer that may be used to implement one or more of the methods described herein.

Turning now to FIG. 3 there is shown a block diagram of an exemplary computer 500 that may be used to implement one or more of the methods described herein. The computer 500 may be a standalone computer, or it may be part of a medical navigation system 1000, for example. The computer 500 may be connected to a display or monitor 600 for viewing system information, and an input device 700 for data entry, screen navigation, etc. Examples of a input device 700 include a keyboard, computer mouse or other device that points to or otherwise identifies a location, action, etc., e.g., by a point and click method or some other method. Alternatively, a touch screen (not shown) may be used in place of the input device 700. The monitor 600 and input device 700 communicate with a processor via an input/output device 510, such as a video card and/or serial port (e.g., a USB port or the like).

A processor 520, such as an AMD Athlon 64® processor or an Intel Pentium IV® processor, combined with a memory 530 execute programs to perform various functions, such as data entry, numerical calculations, screen display, system setup, etc. The memory 530 may comprise several devices, including volatile and non-volatile memory components. Accordingly, the memory 530 may include, for example, random access memory (RAM), read-only memory (ROM), hard disks, floppy disks, optical disks (e.g., CDs and DVDs), tapes, flash devices and/or other memory components, plus associated drives, players and/or readers for the memory devices. The processor 520 and the memory 530 are coupled using a local interface (not shown). The local interface may be, for example, a data bus with accompanying control bus, a network, or other subsystem.

The memory may form part of a storage medium for storing information, such as application data, screen information, programs, etc., part of which may be in the form of a database. The storage medium may be a hard drive, for example, or any other storage means that can retain data, including other magnetic and/or optical storage devices. A network interface card (NIC) 540 allows the computer 500 to communicate with other devices. Such other devices may include a detection device 400.

A person having ordinary skill in the art of computer programming and applications of programming for computer systems would be able in view of the description provided herein to program a computer system 500 to operate and to carry out the functions described herein. Accordingly, details as to the specific programming code have been omitted for the sake of brevity. Also, while software in the memory 530 or in some other memory of the computer and/or server may be used to allow the system to carry out the functions and features described herein in accordance with the preferred embodiment of the invention, such functions and features also could be carried out via dedicated hardware, firmware, software, or combinations thereof, without departing from the scope of the invention.

Computer program elements of the invention may be embodied in hardware and/or in software (including firmware, resident software, micro-code, etc.). The invention may take the form of a computer program product, that can be embodied by a computer-usable or computer-readable storage medium having computer-usable or computer-readable program instructions, "code" or a "computer program" embodied in the medium for use by or in connection with the instruction execution system. In the context of this document, a computer-usable or computer-readable medium may be any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium such as the Internet. Note that the computer-usable or computer-readable medium could even be paper or another suitable medium, upon which the program is printed, as the program can be electronically captured, via, for instance, optical scanning of the paper or other medium, then compiled, interpreted, or otherwise processed in a suitable manner. The computer program product and any software and hardware described herein form the various means for carrying out the functions of the invention in the example embodiments.

Although the invention has been shown and described with respect to a certain preferred embodiment or embodiments, it is obvious that equivalent alterations and modifications will occur to others skilled in the art upon the reading and understanding of this specification and the annexed Figures. For example, regard to the various functions performed by the above described elements (components, assemblies, devices, software, computer programs, etc.), the terms (including a reference to a "means") used to describe such elements are intended to correspond, unless otherwise indicated, to any element that performs the specified function of the described element (i.e., that is functionally equivalent), even though not structurally equivalent to the disclosed structure that performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for determining the position of correspondence object pairs including A-objects and B-objects that represent the same objects of the same anatomical body structure in two different reference frames A and B, comprising:
- defining A-objects that each represent different objects of the body structure in the reference frame A;
- defining B-objects that each represent different objects of the body structure in the reference frame B;
- determining geometric relationship data A that describes a geometric relationship between the A-objects based on positions of the A-objects in the reference frame A;
- determining geometric relationship data B that describes a geometric relationship between the B-objects based on positions of the B-objects in the reference frame B;
- comparing the geometric relationship data A or data derived therefrom with the geometric relationship data B or data derived therefrom; and
- determining a level of correspondence between the A-objects and the B-objects based on the comparison.

2. The method according to claim 1, further comprising:
manipulating at least one A-object and/or B-object based on said comparison and/or based on at least one of the geometric relationship data A and the geometric relationship data B.

3. The method according to claim 2, wherein manipulating at least one A-object and/or B-object comprises at least one of the following:
- checking the position of at least one A-object or B-object;
- adjusting, changing, or correcting the position of at least one A-object or B-object;
- replacing at least one A-object or B-object; and
- automatically calculating the position of at least one new A-object or B-object.

4. The method according to claim 2, wherein a portion of said A-objects and/or said B-objects are automatically selected based on their positions in said geometric relationship data A and said geometric relationship data B for which said comparison achieves an optimal level of correspondence.

5. The method according to claim 1, further comprising:
- providing three-dimensional scaled virtual body structure data based on a medical analysis method in reference frame A, from which the positions of the A-objects can be determined; and
- providing actual body structure data in reference frame B that is captured using a capture device.

6. The method according to claim 1, further comprising:
- changing the position of one of the A-objects or B-objects; and/or
- replacing one of the A-objects or B-objects with a different A-object or B-object, respectively; and
- determining a resulting changed geometric relationship data A and/or a changed geometric relationship data B.

7. The method according to claim 6, wherein the steps of
a) changing the position of one of the A-objects or B-objects and
b) replacing one of the A-objects or B-objects with a new one are repeated to improve the level of correspondence.

8. The method according to claim 1, further comprising:
outputting the correspondence level; and
wherein if the level of correspondence does not meet a predetermined value, proceed to defining, enabling, and/or requesting a position of a new A-object and/or B-object.

9. The method according to claim 1, further comprising:
automatically comparing a geometric relationship between at least two A-objects to a geometric relationship between at least two B-objects based on said geometric relationship data A and said geometric relationship data B and calculating a comparative value.

10. The method according to claim 9, wherein calculating a comparative value comprises:
- determining at least two auxiliary objects; and
- comparing said at least two auxiliary objects to each other; and/or
- using said at least two auxiliary objects in subsequent calculations.

11. The method according to claim 10, wherein said auxiliary objects are defined by fitting and/or placing geometric structures onto parts of the anatomical body structure and/or onto A-objects and/or B-objects.

12. The method according to claim 9, wherein a comparative value is selected from a plurality of comparative values that are based on different geometric relationships between said positions of A-objects in said framework A and/or said positions of B-objects in said framework B.

13. The method according to claim 9, further comprising determining an auxiliary object based on said comparative value.

14. The method according to claim 1, further comprising:
wherein if the level of correspondence does not meet a predetermined value, then at least one of the following steps is performed:
- outputting the level of correspondence;
- defining a new A-object in said reference frame A and/or defining a new B-object in said reference frame B, wherein the new A-object replaces a previously defined A-object and/or the new B-object replaces a previously defined B-object;
- automatically changing the position of an A-object in said reference frame A and/or a changing the position of a B-object in said reference frame B; and
- automatically replacing a previously defined A-object with a different A-object and/or automatically replacing a previously defined B-object with a different B-object;
wherein the position of the different A-object and/or different B-object is determined such that a subsequent comparison provides a better level of correspondence than when the comparison was based on the previously defined A-object and/or B-object.

15. The method according to claim 1, further comprising computing a measure of consistency of the positions of the correspondence object pairs based on positions in said geometric relationship data A and said geometric relationship data B.

16. The method according to claim 15, wherein said measure of consistency of the positions of the correspondence object pairs is determined by automatically comparing said geometric relationship data A to said geometric relationship data B and automatically calculating comparative values.

17. The method according to claim 1, further comprising calculating a comparative value, comprising:
- transforming and/or projecting A-objects and/or B-objects and/or auxiliary objects into a common coordinate space, that enables a comparison of the transformed and/or projected objects, and
- comparing shape, dimensions, and/or geometric relationship data associated with of the transformed and/or projected objects in said common coordinate space.

18. The method according to claim 1, wherein said geometric relationship data A and said geometric relationship data B include at least one of the following relationships:
- the distance relationship between two objects;
- angular relationships between connecting lines that connect objects;
- angular relationships between planes defined by three or more objects;

the distance between an object and a projection of the object onto a connecting line and/or into a plane;

angular relationships that result from projections of an object onto a connecting line or a plane.

19. The method according to claim 1, further comprising: manually determining the positions of correspondence object pairs based on the defined A-objects and B-objects using an input device and/or a capture device.

20. The method according to claim 1, further comprising: automatically determining positions of correspondence object pairs based on said geometric relationship data A and said geometric relationship data B.

21. The method according to claim 20, further comprising: automatically aligning parts of the anatomical body structure and/or some of the objects based on the determined positions of the correspondence object pairs; and calculating a comparative value.

22. The method according to claim 1, further comprising: determining a partial spatial relationship between the two reference frames A and B based on the correspondence object pairs, and providing reference information that indicates the possible position in one reference frame of an object the corresponds to an object that has been defined in the other reference frame, based on said partial spatial relationship between the two reference frames A and B.

23. The method according to claim 1, wherein reference frame A is one of a virtual reference frame or an actual reference frame, and reference frame B is the other of the virtual reference frame or the actual reference frame.

24. The method according to claim 23, wherein the virtual reference frame is a reference frame in computer space, and the actual reference frame is a reference frame in patient space.

25. A computer program embodied on a non-transitory computer readable medium for determining the position of correspondence object pairs including A-objects and B-objects that represent the same objects of the same anatomical body structure in two different reference frames A and B, comprising:

code for defining A-objects that each represent different objects of the body structure in the reference frame A;

code for defining B-objects that each represent different objects of the body structure in the reference frame B;

code for determining geometric relationship data A that describes a geometric relationship between the A-objects based on positions of the A-objects in the reference frame A;

code for determining geometric relationship data B that describes a geometric relationship between the B-objects based on positions of the B-objects in the reference frame B;

code for comparing the geometric relationship data A or data derived therefrom with the geometric relationship data B or data derived therefrom; and code for determining a level of correspondence between the A-objects and the B-objects based on the comparison.

26. A system for determining the position of correspondence object pairs including A-objects and B-objects that represent the same objects of the same anatomical body structure in two different reference frames A and B, comprising:

a computer operatively coupled to receive a three-dimensional imaging data set of an anatomical body structure, said computer comprising:

a processor and memory, and logic stored in the memory and executable by the processor, said logic including:

i) logic that defines A-objects that each represent different objects of the body structure in the reference frame A;

ii) logic that defines B-objects that each represent different objects of the body structure in the reference frame B;

iii) logic that determines geometric relationship data A that describes a geometric relationship between the A-objects based on positions of the A-objects in the reference frame A;

iv) logic that determines geometric relationship data B that describes a geometric relationship between the B-objects based on positions of the B-objects in the reference frame B;

v) logic that compares the geometric relationship data A or data derived therefrom with the geometric relationship data B or data derived therefrom; and vi) logic that determines a level of correspondence between the A-objects and the B-objects based on the comparison.

27. The system according to claim 26, further comprising a capture device for capturing the position of actual objects in said reference frame A or reference frame B.

28. The system according to claim 27, wherein the computer further comprises logic that determines the positions of correspondence object pairs based on the defined A-objects and B-objects.

29. The system according to claim 27, further comprising an instrument equipped with an instrument marker device configured to be tracked by the capture device, wherein the computer further comprises logic to determine the position of the instrument marker device in the virtual reference frame on the basis of the determined correspondence object pairs.

* * * * *